United States Patent [19]

Heath

[11] Patent Number: 5,698,721
[45] Date of Patent: Dec. 16, 1997

[54] CATONIC AMPHIPHILES

[75] Inventor: Timothy D. Heath, Madison, Wis.

[73] Assignee: Megabios Corporation, San Francisco, Calif.

[21] Appl. No.: 245,737

[22] Filed: May 18, 1994

Related U.S. Application Data

[63] Continuation-in-part of Ser. No. 153,185, Nov. 15, 1993, abandoned, which is a continuation-in-part of Ser. No. 991,935, Dec. 17, 1992, abandoned.

[51] Int. Cl.$^6$ .................................................. C07F 9/02
[52] U.S. Cl. ........................... 554/80; 574/858; 574/450; 530/387.1
[58] Field of Search ..................... 554/80; 514/85.8, 514/450; 550/387.1

[56] References Cited

PUBLICATIONS

Bruizik et al., J. Org. Chem., vol 51, 1986, pp. 2368–70.
Law et al., (1986) "Use of Phosphotriester Syntetic Methods for Preparation of Phosphatidylethanolamine–Analyte Conjugates" *Tetrahedron Letters*, 27:271–274.
Bruzik et al. (1986) "A general Method for the Synthesis of Glycerophospholipis" *J. Org. Chem.*, 51:2368–2370.
Brigham et al. (1989) "Rapid Communication: In Vivo Transfection of Murine Lungs with a Functioning Prokaryotic Gene using a Liposome Vehicle" *Am. J. Med. Sci.*, 298: 278–281.
Hazinski et al. (1991) "Localization and Induced Expression of Fusion Genes in the Rat Lung" *Am. J. Resp. Cell Molec. Biol.*, 4: 206–209.
Wu and Wu (1988) "Receptor-mediated Gene Delivery and Expression In Vivo" *J. Biol. Chem.*, 263: 14621–14624.
Canonico et al. (1991) "Expression of a CMV Promoter Driven Human alpha–1 Antitrypsin Gene ... " *Clinical Research* 39: 219A.
Stribling et al. (1992) "Aerosol Gene Delivery In Vivo" *Proc. Natl. Acad. Sci. (USA)* 89: 11277–11281.
Yoshimura et al. (1992) "Expression of the Human Cystic Fibrosis Transmembrane Conductance Regulator Gene in the Mouse Lung" *Nuclecic Acids Research*, 20: 3233–3240.
Malone et al. (1989) "Cationic Liposome–mediated RNA Transfection" *Proc. Natl. Acad. Sci. (USA)*, 86: 6077–6081.
Debs et al. (1990) "Regulation of Gene Expression In Vivo by Liposome–mediated Delivery of a Purified Transcription Factor" *J. Biol. Chem.*, 265: 10189–10192.
Straubinger and Papahadjopoulos (1983) "Liposomes as Crriers for Intracellular Delivery of Nucleic Acids" *Methods of Enzmology*, 101: 512 –527.
Olson et al. (1979) "Preparation of Liposomes of Defined Size Distribution by Extrusion Thuough Polycarbonate Membranes" *Biochem. Biophys. Acta.*, 557: 9–23.
Nabel et al. (1990) "Site–Specific Gene Expression In Vivo by Direct Gene Transfer into the Arterial Wall" *Science*, 249: 1285–1288.
Wolff et al. (1990) "Direct Gene Transfer into Mouse Muscle In Vivo" *Science*, 247: 1465–1468.
Wang and Huang (1987) "pH–Sensitive Immunoliposomes Mediate Target–Cell–Specific Delivery and Controlled Expression of a Foreign Gene in Mouse" *Proc. Natl. Acad. Sci. (USA)*, 84: 7851–7855.
Felgner et al. (1987) "Lipofection: A Highly Efficient, Lipid–mediated DNA–transfection Procedure" *Proc. Natl. Acad. Sci. (USA)*, 84: 7413–7416.

*Primary Examiner*—Jose'G. Dees
*Assistant Examiner*—Deborah D. Carr
*Attorney, Agent, or Firm*—McDonnell Boehen Hulbert & Berghoff

[57] ABSTRACT

Cationic amphiphiles are provided that are alkyl or alkoxyalkyl O-phosphate esters of diacylphosphatidyl zwitterionic compounds such as phosphatidylcholine or phosphatidyl ethanolamine. The amphiphiles can be used as carriers for delivering macromolecules intracellularly.

12 Claims, No Drawings

CATIONIC AMPHIPHILES

CROSS-REFERENCE TO RELATED APPLICATIONS

This application is a continuation-in-part of U.S. Ser. No. 08/153,185, filed Nov. 15, 1993, now abandoned, which is a continuation-in-part of U.S. Ser. No. 07/991,935, filed Dec. 17, 1992, now abandoned, both of which disclosures are herein incorporated by reference.

INTRODUCTION

1. Field of Invention

The invention relates to cationic amphiphiles that are biodegradable to non-toxic components for use in the preparation of liposomes and other lipid-containing carriers of pharmaceutical substances, including nucleic acids used in gene therapy. The cationic amphiphiles are exemplified by derivatives of phosphatidylcholine and phosphatidylethanolamine.

2. Background

Liposomes are one of a number of lipid-based materials used as biological carriers and have been used effectively as carriers in a number of pharmaceutical and other biological situations, particularly to introduce drugs, radiotherapeutic agents, enzymes, viruses, transcriptional factors and other cellular vectors into a variety of cultured cell lines and animals. Successful clinical trials have examined the effectiveness of liposome-mediated drug delivery for targeting liposome-entrapped drugs to specific tissues and specific cell types. See, for example, U.S. Pat. No. 5,264,618, which describes a number of techniques for using lipid carriers, including the preparation of liposomes and pharmaceutical compositions and the use of such compositions in clinical situations. However, while the basic methodology for using liposome-mediated vectors is well developed, improvements in the materials used in the methods, both in terms of biocompatability and in terms of effectiveness of the carrier process, are still desirable.

In particular, the expression of exogenous genes in humans and/or various commercially important animals will ultimately permit the prevention and/or cure of many important human diseases and the development of animals with commercially important characteristics. Genes are high molecular weight, polyanionic molecules for which carrier-mediated delivery usually is required for DNA transfection of cells either in vitro or in vivo. Therefore it is of interest to develop lipid transfection vectors which will enhance both the delivery and the ultimate expression of the cloned gene in a tissue or cell of interest. Since in some instances a treatment regimen will involve repeated administration of a gene (or other pharmaceutical product), it also is of interest that the lipid carriers be nontoxic to the host, even after repeated administration.

Relevant literature

Amphiphilic phosphatidylethanolamine conjugates for functionalization of liposomes are disclosed in Law et al., (1986) *Tetrahedron Letters*, 27:271-274. A method for synthesis of 1,2-dipalmitoyl-SN-glycero-3-phosphoester is disclosed in Bruzik et al., (1986) *J. Org. Chem.*, 51:2368-23270. The o-methyl ester of dipalmitoyl phosphatidylcholine was prepare as an intermediate in this synthesis.

Use of liposomes as carriers for DNA is described in a number of publications, including the following: Friedmann, (1989) *Science*, 244:1275-1281; Brigham et al., (1989) Am.  J. Med. Sci., 298:278-281; Nabel et al., (1990) *Science*, 249:1285-1288; Hazinski et al., (1991) *Am. J. Resp. Cell Molec. Biol.*, 4:206-209; and Wang and Huang, (1987) *Proc. Natl. Acad. Sci.* (USA), 84:7851-7855. Other publications relating to liposomes describe liposomes coupled to ligand-specific, cation-based transport systems (Wu and Wu, (1988) *J. Biol. Chem.*, 263:14621-14624) or the use of naked DNA expression vectors (Nabel et al., (1990) *Science*, 249: 1285-1288); Wolff et al., (1990) *Science*, 247:1465-1468).

The Brigham et al. group [*Am. J. Med. Sci.* (1989) 298:278-281 and *Clinical Research* (1991) 39 (abstract)] have reported in vivo transfection of lungs of mice following either intravenous or intratracheal administration of a DNA liposome complex. See also Stribling et al., (1992) *Proc. Nat'l Acad. Sci. USA* 89:11277-11281, which reports the use of liposomes as carriers for aerosol delivery of transgenes to the lungs of mice, and Yoshimura et al. (1992) *Nucleic Acids Research* 20:3233-3240.

Cationic lipid carriers have been reported to mediate intercellular delivery of plasmid DNA (Felgner et al., *Proc. Nat'l. Acad. Sci. USA* (1987) 84:7413-7417); mRNA (Malone and Keloff, *Proc. Nat'l. Acad. Sci. USA* (1989) 86:6077-6081); and purified transcription factors (Debs et al., *J. Biol. Chem.* (1990) 265: 10189-10192) in functional form.

SUMMARY OF THE INVENTION

Biodegradable cationic amphiphiles are provided together with methods for their use. The amphiphiles are prepared from naturally occurring, synthetic or semi-synthetic phosphoglycerides by modification of the phosphate moiety of the phosphoglyceride with a neutral group. The cationic amphiphiles are capable of forming complexes with nucleic acids, and other biological compounds and the nucleic acid complexes are capable of transforming mammalian cells. The amphiphiles of the invention yield non-toxic degradation products when subjected to endogenous enzymatic processes.

DESCRIPTION OF SPECIFIC EMBODIMENTS

Metabolizable cationic amphiphilic materials are provided which are useful as carriers for biologically active molecules, such as antibiotics or nucleic acids used in cell transformation processes. The use of the cationic amphiphiles as nucleic acid carriers is described in detail, since the compositions prepared using the amphiphiles are particularly efficacious for this purpose. However, the amphiphiles are also useful in standard drug delivery regimens, such as for the delivery of antibiotics to the lungs of a patient. In particular, complexes of the amphiphiles with DNA (for the transformation of cells in mammalian tissues) give rise to reduced amounts of toxic cleavage products when subject to the metabolic degradation process.

The invention in particular is directed to phosphorus-containing cationic amphiphiles which are nontoxic themselves and which yield by-products, such as those produced by enzymatic cleavage, which are nontoxic to a host organism or which are identical to substances endogenous to a host organism. These amphiphiles thus offer the advantage that they can readily be used in humans, since they can be used repeatedly without the accumulation of toxic by-products.

It will be apparent that the cations of the invention must be present in association with one or more anions, e.g., hydroxide, chloride, or bromide ions or more complex organic anions or bases. The particular anion associated with an amphiphilic cation is not critical to the formation or utility of the amphiphilic cation and may exchange (in whole or part) for other anions during use of the composition. Accordingly, the amphiphilic compounds of the invention are described in this specification generally in terms of the cation without reference to any particular anion. However, a number of specific examples are given, as well as general guidance for selection of anions. For human administration, chloride is the preferred anion; also acceptable are bromide or other physiologically acceptable anions including acetate, succinate and citrate.

The cationic amphiphiles of the invention are diacylphosphatidyl derivatives of the formula

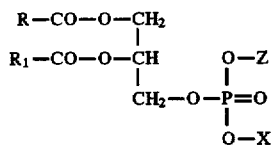

wherein

Z is alkyl or alkoxyalkyl of 1 to 6 carbon atoms inclusive,

R and $R_1$ independently are straight-chain, aliphatic groups of from 11 to 29 carbon atoms inclusive, and X is a cationic moiety of the formula

wherein n is an integer from 1 to 4 inclusive and $R_2$ independently is hydrogen or a lower alkyl of 1 to 4 carbon atoms inclusive.

Preferred diacylphosphatidyl derivatives of formula I are those in which Z is alkyl. Also preferred are those derivatives in which R and $R_1$ independently are the alkyl or alkenyl portions of naturally occurring fatty acids containing from 14 to 24 carbon atoms inclusive (i.e., R—COOH, for example, would be the corresponding fatty acid of R—). Also preferred are those cations in which n is 1. The compound O-methyl dipalmitoylphosphatidylcholine is specifically excluded from compound coverage of the present invention as it was prepared as an intermediate during the synthesis of 1,2-dipalmitoyl-SN-glycero-3-phosphoester as disclosed in Bruzik et al., (1986) *J. Org. Chem.*, 51:2368–23270. However, the use of such a compound as a biological carrier was not disclosed, and the use of O-methyl dipalmitoylphosphatidylcholine as a biological carrier is within the scope of methods of the present invention.

The cationic amphiphiles of formula I are O-substituted phosphate esters of the corresponding acidic or zwitterionic diacylphosphatidyl compounds and, in one production technique, can readily be produced from the corresponding compounds, many of which are commercially available. The acidic and zwitterionic amphiphilic compounds are illustrated by a number of known choline derivatives of the formula

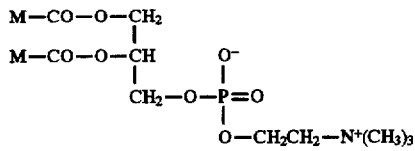

wherein each M together with the carboxyl group to which it is attached is derived from a fatty acid moiety. The compounds of formula III are zwitterionic in character and exhibit acidic properties resulting from the presence of the phosphate group. In contrast, the O-esters of formula I are cationic, as esterification of the phosphate oxygen eliminates the negative charge on the phosphate oxygen.

In the cationic amphiphiles of formula I, each of R and $R_1$ together with the carboxyl group to which they are attached are obtainable from straight-chain, aliphatic, hydrocarboxylic acid moieties of from 12 to 30 carbon atoms inclusive, preferably from 15 to 25 carbon atoms inclusive. Such carboxylic acid moieties are commonly referred to as fatty acid moieties because of their presence in natural fats. The acid moieties are saturated or ethylenically unsaturated, and within the cations of formula I R and R, are the same or are different. Illustrative fatty acid moieties are lauroyl, myristoyl, palmitoyl, stearoyl, linoleoyl, tridecanoyl and oleoyl fatty acids. In an embodiment of the invention in which the cationic amphiphiles are prepared synthetically, it is advantageous for R and $R_1$ to be the same. Alternatively, when a composition of the invention is prepared from naturally occurring materials, the R and R moieties often will be different.

Suitable Z groups are derived from alkanols or alkoxyalkanols which are straight-chain or branched. Illustrative Z groups include methyl, ethyl, propyl, isopropyl, n-butyl, sec-butyl, pentyl, hexyl, 2-methoxyethyl, 3-ethoxypropyl, and 3-methoxypropyl. Preferred Z groups are straight-chain alkyl groups, and more preferably the Z group is methyl or ethyl, especially ethyl.

Suitable X groups, illustrative by formula because of the complexity of the nomenclature, include the following:

—$CH_2$—$CH_2$—$N^+(CH_3)_3$
—$CH_2$—$CH_2$—$N^+H_3$
—$CH_2$—$CH_2$—$CH_2$—$N^+(CH_3)_2(CH_2CH_3)$
—$CH_2$—$CH_2$—$N^+H_2(CH_3)$
—$CH_2$—$CH_2$—$CH_2$—$N^+(CH_3)_3$
—$CH_2$—$CH_2$—$N^+H(CH_3)_2$

Preferred X groups are those in which n is 1 and each $R_2$ independently is hydrogen or methyl.

The nomenclature of the cationic amphiphiles of the invention is also rather complex, but the structures of cations within the scope of the invention will be apparent from the above formula I and the definitions of the terms as provided. In general, the cationic amphiphiles are O,O'-esters of a diacylphosphatidyl acid where X and Z are the esterifying groups. By analogy to the conventional nomenclature for the materials of formula III, the X group is designated in terms of the hydroxylic compound from which it is derived. Thus, in cations wherein X is cholinyl, i.e., —$CH_2$—$CH_2$—$N^+$(CH$_3$)$_3$, the cations are O-alkyl or O-alkoxyalkyl esters of a diacylphosphatidylcholine. In similar manner, an O-ester of a diacylphosphatidyl acid derivative in which X is —$CH_2$—$CH_2$—$NH_2$ is referred to as a O-alkyl ester of a diacylphosphatidylethanolamine. By way of specific illustration, the cationic amphiphile of the formula

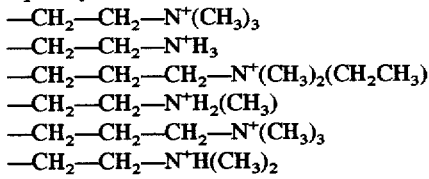

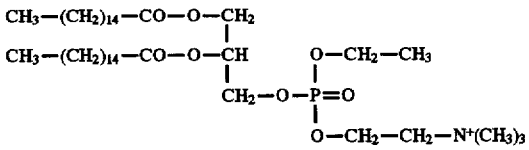

is O-ethyl dipalmitoylphosphatidylcholine. The cationic amphiphile of the formula

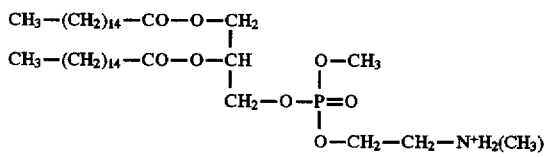

is a methyl quaternary ammonium derivative of O-methyl dipalmitoylphosphatidylethanolamine.

Cationic amphiphiles of formula I are produced by conventional synthetic processes. For example, a zwitterionic diacylphosphatidyl acid, e.g., a diacylphosphafidylcholine, is esterified by a substantially equimolar quantity of the hydroxylic compound from which Z is derived, e.g., methanol. In practice, esterification is facilitated by the presence of a sulfonyl halide such as methanesulfonyl chloride or p-toluenesulfonyl chloride as well as an organic base such as pyridine, picoline or lutidine. The methyl, ethyl, propyl, and butyl derivatives of dimyristoyl, dipalmitoyl, distearoyl, and egg (a mixture of acyl groups) phosphatidyl choline can all be prepared using this method.

Alternatively, a synthesis can be carried out in which the diacylphosphatidyl reactant is a compound where the X alcohol moiety is derived from an uncharged amino alcohol, e.g.,

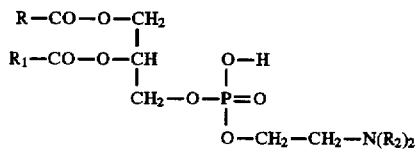

Such amine alcohol derivatives, which may be at least partially zwitterionic in character as a result of protonization during or before the actual synthesis steps, are also contacted with the desired alcohol, sulfonylhalide and base to produce the desired O-ester. However, if any $R_2$ group is hydrogen, it is necessary to "protect" the amine function by introducing a bulky "shielding" group to prevent reaction of amino hydrogen during the esterification process. Such protection is conventional and typically comprises reaction of the amine group with triphenylmethyl chloride (trityl chloride) or t-butoxycarbonyl chloride (BOC). Subsequent to esterification, the protecting group is removed by conventional procedures such as hydrolysis. The O-ester corresponding to the compound of formula VI, if not protonated during its production, is converted to the quaternary ammonium cation of formula I by subsequent conventional protonation or reaction with an alkyl halide such as methyl bromide.

Among the naturally occurring lipids which can be employed for preparation of the cationic amphiphiles are phosphatidyl compounds, such as phosphatidyl choline (PC) and phosphatidyl ethanolamine (PE), and sphingolipids such as sphingomyelin.

The cationic lipids of the invention are typically used as carriers for various biological molecules, such as antibiotics or nucleic acids. In particular, the cationic lipids can be used alone or combined with other lipids in formulations for the preparation of lipid vesicles or liposomes for use in intracellular delivery systems. Uses contemplated for the lipids of the invention include transfection procedures corresponding to those presently known that use amphiphilic lipids, including those using commercial cationic lipid preparations, such as Lipofectin™, and various other published techniques using conventional cationic lipid technology and methods.

The cationic lipids of the invention can be used in pharmaceutical formulations to deliver therapeutic agents by various routes and to various sites in an animal body to achieve a desired therapeutic affect.

Because such techniques are generally known in the art, background information and basic techniques for the preparation of pharmaceutical compositions containing lipids will not be repeated at this time. A reader unfamiliar with this background information is referred to the publications under the heading Relevant Literature above and further to U.S. Pat. No. 5,264,618. This last-cited patent describes a number of therapeutic formulations and methods in detail, including examples of the use of specific cationic lipids (different from those described here) that can be followed in detail by substituting the cationic lipids of the present invention for those described in the patent. Compositions of the present invention will minimally be useable in the manner described in the patent, although operating parameters may need to be modified in order to achieve optimum results, using the specific information provided for compounds of the invention in this specification along with the knowledge of a person skilled in the arts of lipid preparation and use.

The lipids of the present invention have been shown to be particularly useful and advantageous in the transfection of animal cells by genetic material. Additionally, since these compositions are degraded by enzymatic reactions in animal cells to components that are typically indigenous to the cells, the compositions provide a number of advantages in the area of low toxicity when compared to previously known cationic lipids. These and other advantages of the invention are discussed in detail below. The remainder of this discussion is directed principally to selection, production, and use parameters for the cationic lipids of the present invention that may not immediately be apparent to one of ordinary skill in the art.

Particularly where it is desirable to target a lipid-DNA complex to a particular cell or tissue, a lipid mixture used as a carrier can be modified in a variety of ways. By a lipid mixture is intended a formulation prepared from the cationic amphiphile of the invention, with or without additional agents such as steroids, and includes liposomes, interleaved bilayers of lipid, and the like. Steroids, e.g. cholesterol or ergosterol, can be used in combination with the cationic amphiphiles when used to prepare mixtures. In some embodiments, the lipid mixture will have from 0–67 mole percent steroid, preferably about 33 to 50 mole percent steroid. A lipid-DNA complex is the composition obtained following combination of DNA and a lipid mixture. Non-lipid material (such as biological molecules being delivered to an animal or plant cell or target-specific moieties) can be conjugated through a linking group to one or more hydrophobic groups, e.g. using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains, which will allow for their association with the lipid mixture without covalent linking to one or more lipid groups.

For the most part, the active compounds to be bound to the lipid mixture are ligands or receptors capable of binding to some biological molecule of interest that is present in the target cell. A ligand can be any compound of interest which can specifically bind to another compound, referred to as a receptor, the ligand and receptor forming a complementary pair. The active compounds bound to the lipid mixture can vary widely, from small haptens (molecular weights of about 125 to 2,000) to antigens which will generally have molecular weights of at least about 6,000 and generally less than about 1 million, more usually less than about 300,000. Of particular interest are proteinaceous ligands and receptors that have specific complementary binding partners on cell surfaces. Illustrative active compounds include chorionic gonadotropin, encephalon, endorphin, luteinizing hormone, morphine, epinephrine, interferon, ACTH, and polyiodothyronines and fragments of such compounds that retain the ability to bind to the same cell-surface binding partners that bind the original (non-fragment) molecules.

The number of targeting molecules (either ligand or receptor) bound to a lipid mixture will vary with the size of the liposome, the size of the molecule, the binding affinity of the molecule to the target cell receptor or ligand, and the like. Usually, the bound active molecules will be present in the lipid mixture in from about 0.05 to 2 mole percent, more usually from about 0.01 to 1 mole percent based on the percent of bound molecules to the total number of molecules available in the mixture for binding.

The surface membrane proteins which bind to specific effector molecules (usually soluble molecules in the external environment of the cell) are referred to as receptors. In the present context, receptors include antibodies and immunoglobulins since these molecules are found on the surface of certain cells. However, since antibodies are generally used to bind liposomes to receptor molecules on target cells, the antibodies and immunoglobulins bound to a liposome containing a cationic lipid of the invention can also be considered to be ligands. The immunoglobulins may be monoclonal or polyclonal, preferably monoclonal. Usually the immunoglobulins will be IgG and IgM, although the other immunoglobulins may also find use, such as IgA, IgD, and IgE. The intact immunoglobulins may be used or only fragments thereof, such as Fab, F(ab')$_2$, F$_d$, or F$_v$ fragments as well as a complete light or heavy chain.

For antibodies used as cell-targeting ligands, antibodies of interest are those that bind to surface membrane antigens such as those antigens comprising the major histocompatibility complex, particularly the HLA-A, -B, -C and -D. Other surface antigens include thy-1,leu-5, and Ia.

The cationic amphiphiles are particularly useful as carriers for anionic compounds, particularly polyanionic macromolecules such as nucleic acids. Where the amphiphiles are intended for use in vivo, particularly in vivo in humans, or where it is necessary to use the amphiphiles repeatedly, it is important to screen the carriers for those which are metabolized to non-toxic by-products and which themselves are not toxic or those which are eliminated from the body without degradation. The elimination of such amphiphilic cations from tissues can be demonstrated in animal experiments. An animal, such as a mouse, can be administered one or more doses of material containing between 0.5 and 10 pmole of the lipid to be tested, complexed with an active component (such as DNA) if desired. At various times after administration, the animals are sacrificed, tissues taken, total lipids extracted using an appropriate solvent extraction system, and the total lipid analyzed for the particular cationic lipid or its partial degradation product using, for example, HPLC.

The cationic amphiphiles are positively charged, and a tight charge complex can be formed between a cationic lipid carrier and a polyanionic nucleic acid, resulting in a lipid carrier-nucleic acid complex which can be used directly for systemic delivery to a mammal or mammalian cell. Where delivery is via aerosolization, the charge complex will withstand both the forces of nebulization and the environment within the lung airways and be capable of transfecting lung cells after the aerosolized DNA:lipid carrier complex has been deposited in the lung following intranasal or intraoral delivery of the aerosolized complex.

To evaluate the efficacy of a particular amphiphilic cation for use as a nucleic acid carrier in an aerosolization process, as well as to determine the optimum concentrations of lipid carrier-nucleic acid complexes, involves a two-step process. The first step is to identify lipid carriers and the concentration of lipid carrier-nucleic acid complexes that do not aggregate when the components are combined or during the significant agitation of the mixture that occurs during the nebulization step. The second step is to identify among those lipids that do not aggregate those complexes that provide for a high level of transfection and transcription of a gene of interest in target cells in the lung. These techniques are described in WO/US PCT/US92/11008 filed Dec. 17, 1992, which disclosure is hereby incorporated by reference.

As an example, a reporter gene CAT (which encodes chloramphenicol acetyltransferase) can be inserted in an expression cassette and used to evaluate each lipid carrier composition of interest. The DNA:lipid carrier complexes are mixed in solutions which do not themselves induce aggregation of the DNA:lipid carrier complexes, such as sterile water. The expression cassette (DNA) is mixed together with each of the lipid carriers to be tested in multiple different ratios, ranging as an example from 4:1 to 1:10 (micrograms of DNA to nanomoles of cationic lipid or total lipid, if a lipid mixture is present). Examination of the stability of the resulting mixtures provides information concerning which ratios result in aggregation of the DNA:lipid carrier complexes and are therefore not useful for use in vivo, and which complexes remain in a form suitable for aerosolization. The ratios which do not result in aggregation are tested in animal models to determine which of the DNA:lipid carrier ratios confer the highest level of transgene expression in vivo. For example, for aerosol-based transfection, the optimal DNA:lipid carrier ratios for lipid mixtures such as N-[1-(2,3-dioleyloxy)propyl]-N,N,N-triethylammonium chloride(DOTMA):dioleoylphosphatidylethanolamine(DOPE) (the components of this mixture being present in a 1:1 weight ratio) and dimethyl dioctadecyl ammonium bromide (DDAB):Chol (1:1) are 1 to 1. For O-ethyl egg phosphatidylcholine (E-EPC) or especially O-ethyl dimyristoylphosphatidylcholine (E-DMPC) in a 1:1 weight ratio with cholesterol, the DNA:lipid carrier ratio is preferably in the range of from 1.5:1 to 2:1.

If the cationic amphiphile is used for injection, then it need be evaluated only for whether it is effective for transfection of a target cell.

Particular cells can be targeted by the use of particular cationic lipids for preparation of the lipid-mixture carriers, for example, by the use of E-DMPC to target lung cells preferentially, or by modifying the amphiphiles to direct them to particular types of cells using site-directing molecules. Thus antibodies or ligands for particular receptors may be employed, to target a cell associated with a particular surface protein. A particular ligand or antibody can be conjugated to the cationic amphiphile in accordance with conventional techniques, either by conjugating the site-directing molecule to a lipid for incorporation into the lipid bilayer or by providing a linking group on a lipid present in the bilayer for linking to a functionality of the site-directing compound. Such techniques are well known to those skilled in the art.

The various lipid carrier-nucleic acid complexes wherein the lipid carrier is a liposome are prepared using methods well known in the art. Mixing conditions can be optimized by visual examination of the resultant lipid-DNA mixture to establish that no precipitation occurs. To make the lipid-DNA complexes more visible, the complexes can be stained with a dye which does not itself cause aggregation, but which will stain either the DNA or the lipid. For example, Sudan black (which stains lipid) can be used as an aid to examine the lipid-DNA mixture to determine if aggregation is occurred. Particle size also can be studied with methods known in the art, including electron microscopy, laser light scattering, Coulter™ counting/sizing, and the like. Standard-size beads can be included as markers for determining the size of any liposomes or aggregates that form. By "lipid carrier-nucleic acid complex" is meant a nucleic acid sequence as described above, generally bound to the surface of a lipid carrier preparation, as discussed below. The lipid carrier preparation can also include other substances, such as enzymes necessary for integration, transcription and translation or cofactors. Furthermore, the lipid carrier-nucleic acid complex can include targeting agents to deliver the complex to particular cell or tissue types. Generally, the nucleic acid material is added to a suspension of preformed liposomes which may be multi-lamellar vesicles (MLVs) or small unilamellar vesicles (SUVs), usually SUVs formed by sonication. The liposomes themselves are prepared from a dried lipid film that is resuspended in an appropriate mixing solution such as sterile water or an isotonic buffer solution such as 10mM Tris/NaCl or 5% dextrose in sterile water and sonicated to form the liposomes. Then the preformed lipid carriers are mixed directly with the DNA.

Mixing and preparing of the lipid-DNA complex can be critically affected by the sequence in which the lipid and DNA are combined. Generally, it is preferable (to minimize aggregation) to add the lipid to the DNA at ratios of DNA:lipid of up to 1:2 inclusive (microgram DNA:nanomoles cationic lipid). Where the ratio of DNA:lipid is 1:4 or higher, better results are generally obtained by adding the DNA to the lipid. In either case, mixing should be rapidly achieved by shaking or vortexing for small volumes and by use of rapid mixing systems for large volumes. The lipid carrier and DNA form a very stable complex due to binding of the negatively charged DNA to the cationic lipid carriers. SUVs find use with small nucleic acid fragments as well as with large regions of DNA ($\geq$250kb).

In preparing the lipid carrier-nucleic acid complex for nebulization, care should be taken to exclude any compounds from the mixing solution which promote the formation of aggregates of the lipid carrier-nucleic acid complexes. Large particles generally will not be aerosolized by the nebulizer, and even if aerosolized would be too large to penetrate beyond the large airways. Aggregation of the lipid carrier-nucleic acid complex is prevented by controlling the ratio of DNA to lipid carrier, minimizing the overall concentration of DNA:lipid carrier complex in solution, usually less than 5 mg DNA/8 ml solution, and avoiding the use of chelating agents such as EDTA and/or significant amounts of salt, either of which tends to promote macro-aggregation. The preferred excipient is water, dextrose/water or another solution having low or zero ionic strength. Further, the volume should be adjusted to the minimum necessary for deposition in the lungs of the host mammal, while at the same time taking care not to make the solution too concentrated so that aggregates form. Increasing the volume of the solution is to be avoided if possible due to the need to increase the inhalation time for the host animal to accommodate the increased volume. In some cases, it may be preferable to lyophilize the lipid carrier-nucleic acid complexes for inhalation. Such materials are prepared as complexes as described above, except that a cryoprotectant such as mannitol or trehalose is included in the buffer solution which is used for preparation of the lipid carrier-DNA complexes. Any glucose generally included in such a buffer is preferably omitted. The lipid carrier complex is rapidly freeze-dried following mixing of the lipid and DNA. The mixture can be reconstituted with sterile water to yield a composition which is ready for administration to a host animal.

Where the amphiphiles form liposomes, the liposomes may be sized in accordance with conventional techniques, depending upon the desired size. In some instances, a large liposome injected into the bloodstream of an animal has higher affinity for lung cells as compared to liver cells. Therefore, the particular size range may be evaluated in accordance with any intended target tissue by administering lipid-nucleic acid complexes of varying particle sizes to a host animal and determining the size of particle which provides the desired results.

The cationic amphiphiles complexed with nucleic acid of this invention can be administered in a variety of ways to a host, such as intravenously, intramuscularly, subcutaneously, transdermally, topically, intraperitoneally, intravascularly, by aerosol, following nebulization, and the like. Normally, the amphiphiles will be injected in solution where the concentration of compound bound to or entrapped in the liposome will dictate the amount to be administered. This amount will vary with the effectiveness of the compound being administered, the required concentration for the desired effect, the number of administrations, and the like. In some instances, particularly for aerosol administration, the lipid-DNA complexes can be administered in the form of a lyophilized powder.

Upon administration of the amphiphiles, when a targeting moiety is used, the amphiphiles preferentially bind to a cell surface factor complementary to the compounds bound to the liposome. If no targeting moiety is bound to the liposome, then it binds to cell surface by lipophilic interactions. The liposome normally are transferred into the cell by endocytosis.

The cationic amphiphiles find use for complexing with nucleic acid or protein for transporting these macromolecules in vivo. The nucleic acid can include DNA, RNA, antisense RNA or other antisense molecules. Cationic amphiphiles that form liposomes also find use in drug delivery, where the drug can be entrapped within the liposome or bound to the outside.

The following examples are offered by way of illustration and not by way of limitation.

EXAMPLES

Example 1

Synthesis of Methylphosphatidylcholine

Addition of a methyl group to the phosphate moiety of phosphatidylcholine was carried out as follows. One-hundred mg of egg yolk phosphatidylcholine was placed in a 100 ml round bottom flask in chloroform solution, and the chloroform was removed by evaporation. To the lipid film was added 6 ml of dry N,N-dimethylformamide, 3 ml of dry methanol, and 2.5 ml of dry lutidine. The lipid dissolved readily in the solvent mixture. p-Toluenesulfonyl chloride (1.2 g) was added, which dissolved readily. The mixture was allowed to react for 1 hour at room temperature. The flask was then chilled on ice, and 1 ml of distilled water was added. After 15 minutes, the mixture was transferred to a 1 liter flask, together with 20 ml of ethanol. The solvent was removed by rotary evaporation. The resultant residue was dissolved in 30 ml of chloroform, to which was added 30 ml of methanol and 30 ml of distilled water.

After vigorous shaking, the flask was allowed to stand until the contents separated into a lower chloroform layer and an upper methanol/water layer. The chloroform layer was removed and transferred to a fresh flask. To this solution was added a further 30 ml of methanol and 30 ml of water. Three gm of NaCl was dissolved in the water to aid separation of the phases. The mixture was shaken vigorously, allowed to stand, and the chloroform layer was transferred once more to a fresh flask. 30 ml of methanol and 30 ml of water together with 3 gm of NaCl was added again, the mixture was shaken, and the chloroform layer was removed. The washed phospholipid was evaporated to give a yellow oil, which was dissolved in 15 ml of chloroform. This solution was then applied to a 1.5×10 cm column of silica gel in chloroform. After the sample had been loaded onto the column, the column was washed with 100 ml of chloroform, the eluant being discarded. The solvent was then changed to a mixture of chloroform, methanol, water, and glacial acetic acid, in the proportions 69:27:2.3:1.5 by volume. This mixture will subsequently be referred to as solvent A. The column was eluted with 100 ml of solvent A, and the eluant was collected in eight fractions. Thin layer chromatography of the fractions was carried out using solvent A, and the presence of various compounds was detected first by exposing the plates to iodine vapor, and second by spraying the plates with a phosphate spray. In this solvent system, the original phospholipid had an Rf value of approximately 0.2. Fractions 1–3 contained a single compound with an Rf value of approximately 0.5. Fractions 4–6 appeared to contain some residual phosphatidylcholine. The material in fractions 1–3 did not stain readily for the presence of phosphorus, whereas the residual phosphatidylcholine did stain rapidly upon spraying. After 1–2 hours of development at room temperature, the material in fractions 1–3 did appear blue, especially if the plates were rinsed gently in water to eliminate the intense blue background color. Fractions 1–3 were combined to give a total volume of 40 ml. To this was added 16 ml of methanol and 26 ml of a buffer solution containing 50 mM HEPES pH 7.2 The mixture was shaken and allowed to settle. The lower chloroform layer was removed, and washed twice more with 26 ml of methanol and 26 ml of buffer. The washed chloroform layer was evaporated to dryness to give a solid, which was dissolved in chloroform and methanol in the ratio of 9:1.

Some of the material was dried and dissolved in deuterochloroform. Phosphorus NMR revealed a further splitting of the phosphorus peak owing to the presence of the methyl group. Whereas five peaks were detected in phosphatidylcholine, at least 14 peaks were observed in the methyl derivative. Suspension of a small amount of the methylphosphatidylcholine in aqueous buffer produced a suspension which upon sonication became very clear. When some of this suspension was mixed with a sonicated dispersion of phosphatidylglycerol, a negatively charged phospholipid, it formed a cloudy, aggregated material. This suggests that the lipid is cationic, as anticipated, and that it aggregates with the anionic phospholipid.

Example 2

Synthesis of other alkylphosphatidylcholines

The synthesis described in Example 1 can be successfully applied to making other alkyl derivatives of phosphatidylcholine. By substituting ethanol for methanol, O-ethyl phosphatidylcholine has been prepared. Similarly, by substituting either propanol or butanol for the methanol, O-propyl phosphatidylcholine and O-butyl phosphatidylcholine also have been prepared. Similarly, other derivatives can be prepared by using the corresponding alcohols. Reactivity is reduced as chain length and degree of substitution is increased, and lutidine hydrochloride will precipitate out or crystalize out owing to its reduced solubility in the longer chain alcohols. Reaction with ethanol was allowed to proceed for 2 hours before the addition of water. Reaction with propanol and butanol was allowed to proceed for 24 hours, and the reaction appeared only 70% complete from TLC analysis.

Example 3

Synthesis of Modified Phosphatidylethanolamines

In addition to the methods described above for phosphatidylcholine, a similar approach can be adopted to the modification of several other naturally occurring phospholipids to create degradable cationic amphiphiles. These include phosphatidylethanolamine. For phosphatidylethanolamine, the procedure of Example 1 is followed except that it is preferred to protect the primary amino group of the lipid prior to synthesis, and then to remove the protecting group afterwards.

In accordance with the subject invention, compositions and methods are provided for delivering drugs to a cell. The method minimizes non-specific interaction of the drug with cells other than the targeted cells. By employing weakly acidic drugs, which are substantially impermeable to lipid bilayers, leakage of the drug from the amphiphiles is minimized, so as to minimize non-specific effects of the drug. Furthermore, the drag is efficiently incorporated into the cytosol of the cell, where it will be most effective.

Although the foregoing invention has been described in some detail by way of illustration and example for purposes of clarity of understanding, it will be obvious that certain changes and modifications may be practiced within the scope of the appended claims.

All publications and patent applications cited in this specification are herein incorporated by reference to the same extent as if each individual application or publication was specifically and individually incorporated by reference.

What is claimed is:

1. A cationic amphiphile of the formula:

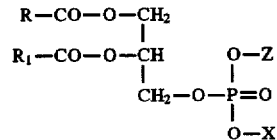

wherein

Z is alkyl or alkoxyalkyl,

R and $R_1$ are the same or different straight-chain, aliphatic hydrocarbyl groups of from 11 to 29 carbon atoms and X is a cationic moiety of the formula

wherein n is an integer from 1 to 4 inclusive and each $R_2$ independently is hydrogen or lower alkyl, with the proviso that when Z is methyl, R and $R_1$ are not both n-pentadecyl.

2. The amphiphile of claim 1 wherein n is 1.
3. The amphiphile of claim 2 wherein $R_2$ is H or methyl.
4. The amphiphile of claim 3 wherein Z is methyl or ethyl.
5. The amphiphile of claim 3 wherein R and $R_1$ are groups of from 14 to 24 carbon atoms inclusive.
6. A cationic amphiphile of the formula

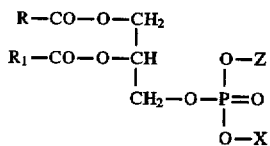

wherein Z is alkyl or alkoxyalkyl,

R and $R_1$ are independently straight-chain, aliphatic hydrocarbyl groups of from 11 to 29 carbon atoms inclusive and X is a cationic moiety of the formula

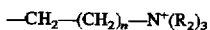

wherein n is an integer from 1 to 4 inclusive and $R_2$ independently is hydrogen or lower alkyl with at least one $R_2$ being hydrogen.

7. The amphiphile of claim 6 wherein n is 1.
8. The amphiphile of claim 7 wherein two $R_2$ moieties are hydrogen.
9. The amphiphile of claim 8 wherein $R_2$ is hydrogen or methyl.
10. The amphiphile of claim 7 wherein Z is methyl or ethyl.
11. The cationic amphiphile according to claim 1, wherein said composition is lyophilized or is in a sonicated suspension or is mixed with cholesterol.
12. The cationic amphiphile according to claim 11, wherein an antibody is bound to said cationic amphiphilie.

* * * * *